US00PP11405P

United States Patent [19]

Usrey

[11] Patent Number: Plant 11,405

[45] Date of Patent: Jun. 6, 2000

[54] *HYDRANGEA MACROPHYLLA* NAMED 'MONREY'

[75] Inventor: William B. Usrey, Dayton, Oreg.

[73] Assignee: Monrovia Nursery Company, Azusa, Calif.

[21] Appl. No.: 08/826,993

[22] Filed: Apr. 11, 1997

[51] Int. Cl.[7] ..... A01H 5/00

[52] U.S. Cl. ..... Plt./250

[58] Field of Search ..... Plt./67.1, 250

*Primary Examiner*—Howard J. Locker
*Assistant Examiner*—Melissa L. Kimball

[57] ABSTRACT

A new and distinct selection of French Hydrangea which shall be referred to hereinafter as *Hydrangea macrophylla* cultivar Monrey. *Hydrangea macrophylla* cultivar Monrey differs distinctively from other *Hydrangea macrophylla* plants by a unique combination of deep pink flower sepals with margins edged white, lustrous deep green foliage and foliage which turns a light burgundy color in cool weather.

1 Drawing Sheet

BACKGROUND OF THE INVENTION

The present invention relates to a new and distinct selection of *Hydrangea macrophylla,* a member of the Saxifragaceae family. *Hydrangea macrophylla* cv. Monrey was the result of a discovery of a naturally occurring branch sport of a proprietary Hydrangea in the test area at Monrovia Nursery Company, 18331 East Foothill Boulevard, Azusa, Calif.

My new discovery has been asexually reproduced vegetatively by cuttings since my discovery in May 1992 at 18331 East Foothill Boulevard, Azusa, Calif. Had this sport not been discovered and propagated it likely would have been lost to mankind. It is unlikely the select and favorable attributes of this plant could be conveyed to progeny through sexual reproduction in the next generation. However, through extensive propagation by rooting of the plant it has been established that the novel exceptional characteristics of this plant are stable and reliably passed on to clonal specimens through asexual reproduction.

SUMMARY OF INVENTION

*Hydrangea macrophylla* cv. Monrey has unusual rose pink flower sepals that are edged in white along the margins. This white margin is different from other *Hydrangea macrophylla* plants which typically possesses solid colored sepals. The overall effect of the white margins which defines each floret is a clean, clear appearance to the inflorescence.

The lustrous deep green foliage is a darker more intense olive green color when compared to other *Hydrangea macrophylla* plants. This deep green enhances the inflorescence by contrasting the colors. Cooler weather promotes a light burgundy color on the upper surface of the foliage. Even Southern California temperatures which rarely go below 35° F. will cause a light burgundy coloring which provides a lovely seasonal change.

My selection is cold hardy to U.S.D.A. Zone 7 which is equivalent to zero degree Farhenheit or a minus 17.8 degrees Celsius.

BRIEF DESCRIPTION OF ILLUSTRATION

The accompanying illustration shows a typical specimen in bloom. The various stages of the inflorescences are displayed. Young florets emerge from buds with a yellow coloring which mature to a deep rose pink. The dark olive green foliage is portrayed and contrasts with the colors of the inflorescence.

BOTANICAL DESCRIPTION

Below is a detailed description of *Hydrangea macrophylla* cv. Monrey, the color terminology is from the British Horticultural Color Charts. Plant grown and observed in Azusa, Calif.

Overall habit: Compact, rounded, deciduous shrub.
Overall size: Height to 1 meter and width 1 to 1.3 meter at five years.
Cold hardiness: Temperature tolerance to 0° Farhenheit or minus 17.8 Celsius.
Growth rate: outdoor nursery conditions.
Cutting to root initiation: four weeks.
Age of salable plant in number one container (3 liters): about 1 year.
Age of salable plant in number five container (16 liters): about 3 years.
Pruning requirements: pruned about two times per year after bloom season.
Bloom season: plants grown outdoors bloom about mid May through mid to late June. Plants have not been forced to bloom.
Foliage:
- *Shape.*—Broadly, elliptic obovate.
- *Texture.*—Coriaceous.
- *Length.*—13–16 cm.
- *Width.*—9–10 cm.
- *Color.*—Upper new growth, Spinach Green 0960/3 to Scheeles Green 860 deepening to Ivy Green 0001060/3 in shade.
- *Fall color.*—Light burgundy.
- *Tip.*—Acuminate to cuspidate.
- *Underside of leaf.*—Spinach Green 0960/2.
- *Base.*—Varying from oblique to cuneate.
- *Margins.*—Crenulate with top one half deeply crenulate.
- *Pubescense.*—Glabrous.

Petiole:
- *Color.*—Scheeles Green 860/3, glabrous.
- *Length.*—0.5–2.0 cm.

Branch color: Light tan.
Inflorescence:
- *Number.*—When in full bloom covering approximately 80% of the foliage.
- *Size.*—16 cm in width.
- *Shape.*—Globose corymb.

*Floret*.—Number: 35 to 48 per inflorescence. Size: 4 cm–5 cm diameter. Sepals: average 2.75 cm long. Type: no sterile florets only fertile florets visible with stamens and styles present. Color: On newly emerging florets: Indian Yellow 6/2. Sepal numbers: consistently 4. Upper side: Claret Rose 021/1. Under side: Rose Opal 022/2. margins are edged with a definite white color which are 2 mm to 1 mm in width. Fragrance: Light, faint, scent.

I claim:

1. A new and distinct selection of *Hydrangea macrophylla* plant as substantially shown and described herein, that is characterized particularly as a novelty by the unique combination of deep pink flower sepals with margins edged white, lustrous deep green foliage and foliage which turns a light burgundy color in cooler weather.

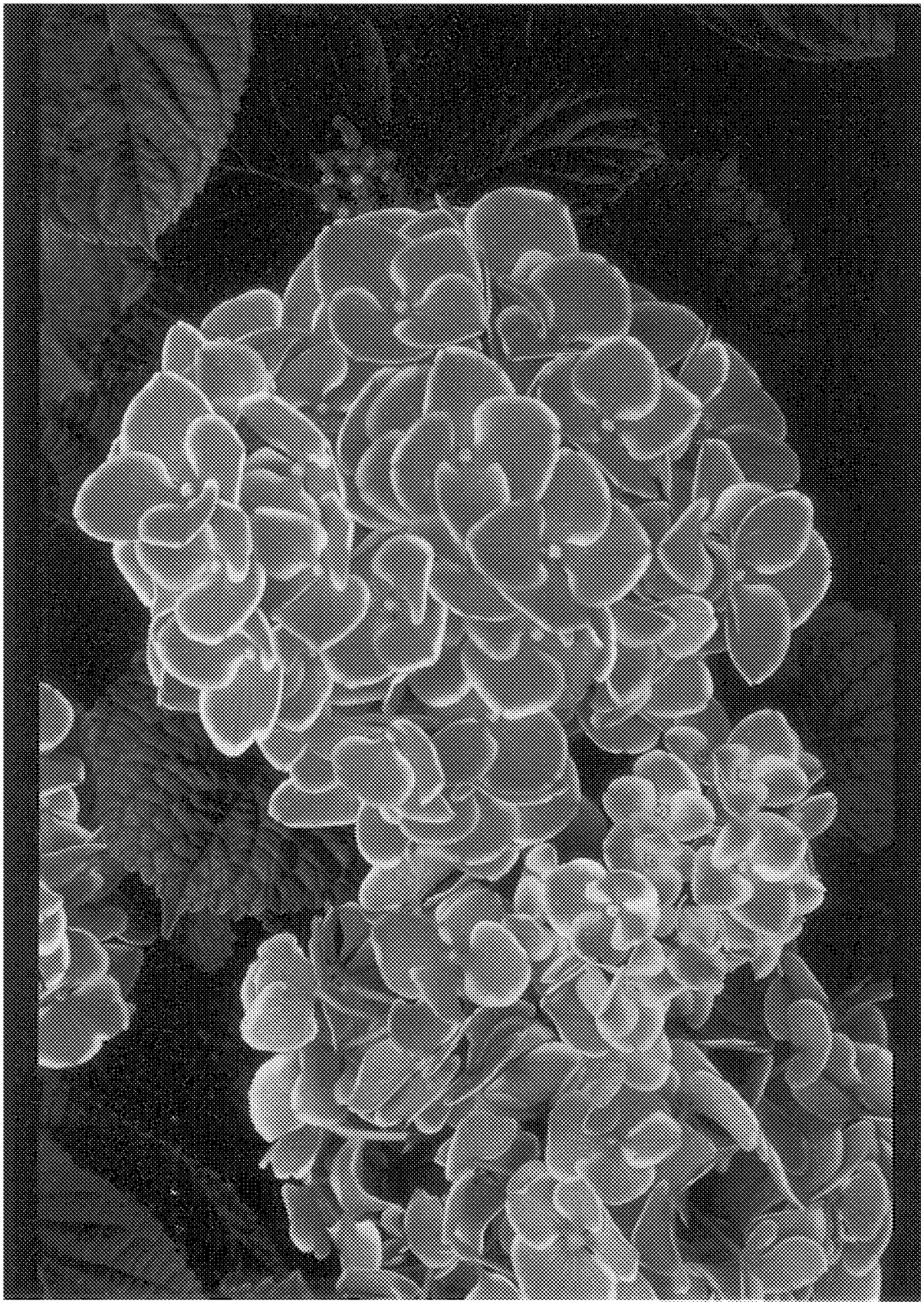

* * * * *